(12) United States Patent
McLaughlin et al.

(10) Patent No.: US 6,365,793 B1
(45) Date of Patent: *Apr. 2, 2002

(54) TOPCOATED ADHESIVE

(75) Inventors: Thomas Lee McLaughlin, Madison; Carol A. Caldwell, Kirtland Hills, both of OH (US)

(73) Assignee: Avery Dennison Corporation, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/341,464

(22) Filed: Nov. 17, 1994

Related U.S. Application Data

(63) Continuation of application No. 08/265,691, filed on Jun. 24, 1994, now abandoned, which is a continuation of application No. 07/881,682, filed on May 12, 1992, now abandoned.

(51) Int. Cl.[7] .......................... A61F 13/15; A61F 13/20
(52) U.S. Cl. .................. 604/359; 604/367; 604/390
(58) Field of Search ................ 604/359, 389, 604/370, 367; 602/54–57, 900, 903; 128/851; 428/40–42, 353–354; 427/259, 402

(56) References Cited

U.S. PATENT DOCUMENTS

| | | | | |
|---|---|---|---|---|
| 3,776,234 A | * | 12/1973 | Hoey | 604/390 |
| 4,299,223 A | * | 11/1981 | Cronkrite | 604/340 |
| 4,801,486 A | * | 1/1989 | Panza et al. | 604/390 |

* cited by examiner

*Primary Examiner*—John G. Weiss
*Assistant Examiner*—K. M. Reichle
(74) *Attorney, Agent, or Firm*—Pearne & Gordon LLP

(57) ABSTRACT

A pressure-sensitive tape substrate is coated with an adhesive, and the adhesive is then printed with an ink or the like that acts as an adhesive-inhibiting masking or barrier along one or more continuous zones or lines. Tapes are formed in whole or in part by slitting along the continuous line or lines so defined. The technique is used to make transfer tapes, diaper fastener tabs, and other products.

2 Claims, 4 Drawing Sheets

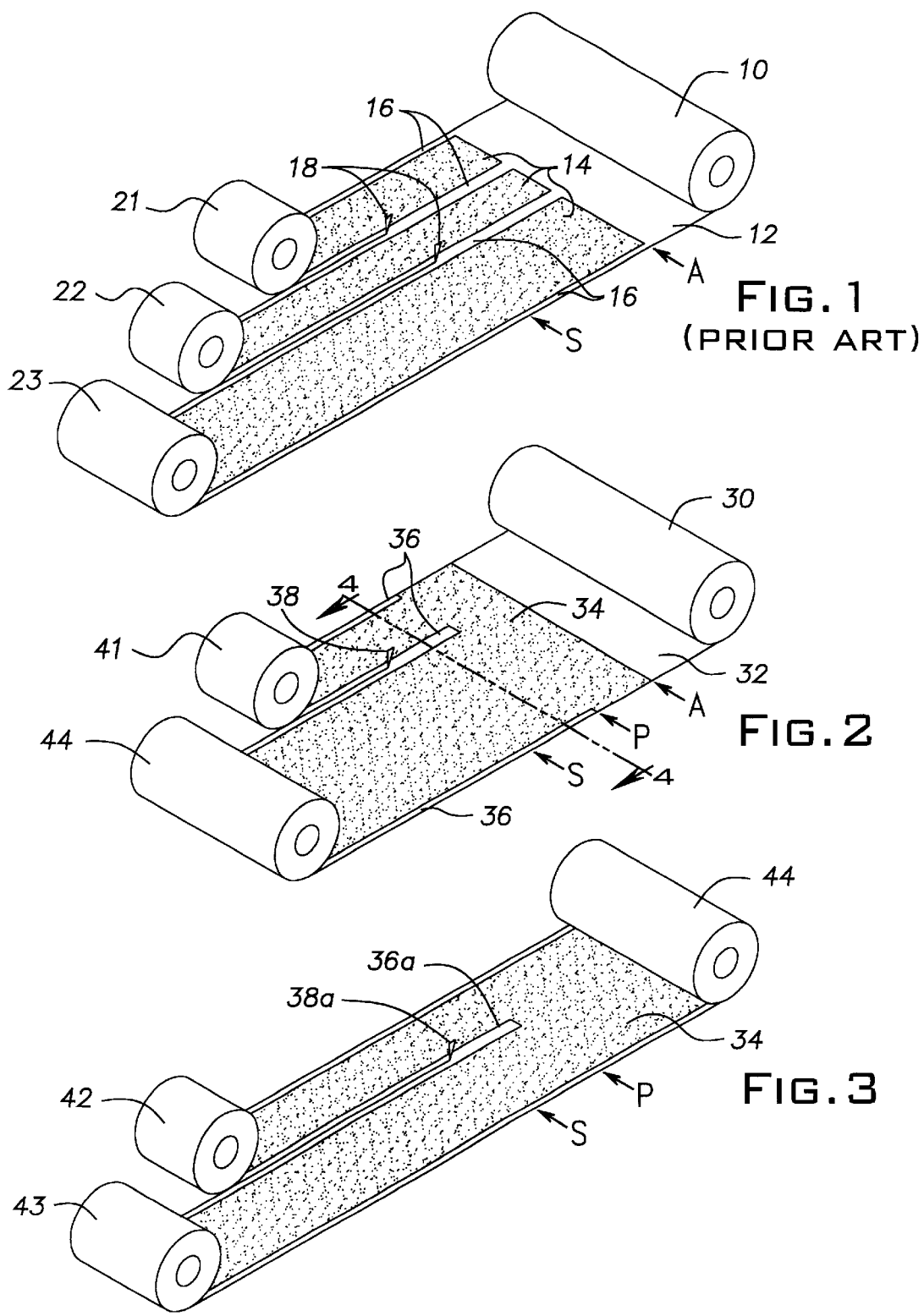

TOPCOATED ADHESIVE

This is a continuation of application Ser. No. 08/265,691, filed Jun. 24, 1994, which is a continuation of application Ser. No. 07/881,682, filed May 12, 1992, both now abandoned.

This invention relates to pressure-sensitive adhesive tapes, adhesive tabs formed therefrom, and methods for manufacturing the same. In one aspect, the invention relates to improvements in transfer tapes and like products, and in the manufacture of the same. In another aspect, the invention relates to improvements in laminate web constructions of diaper fastener-tab stock of the kind adapted to be supplied to a diaper manufacturer and to be separated by the manufacturer into individual diaper-fastening tabs and applied to individual diapers, usually two tabs to a diaper for infant diapers and six tabs to a diaper for adult diapers. In this aspect, the invention particularly relates to means forming part of the diaper tabs and providing novel conveniently manipulated fingerlifts for the tabs.

PRIOR ART

It has been previously proposed to make articles from pressure-sensitive adhesive tapes in which the layer of pressure-sensitive adhesive is partially covered with a printed pattern of ink.

In U.S. Pat. No. 3,159,930 to Allen et al., a pressure-sensitive tape has a layer 5 printed on the adhesive face. This layer combines adhesive masking and indicia functions, the indicia being in the form of negative images in the mask. The masking layer masks most of the adhesive at the centers of the document-containing articles which are to be cut from the tape, but leaves the adhesive exposed at the edges of the articles. The tape is combined with a release liner.

In U.S. Pat. No. 3,874,893 to Cherrin, which is similar to Allen et al., one or more layers of ink or "overprint lacquer" or "a coating which through solvent or other action causes the adhesive to lose most of its adhesive properties" are applied to the adhesive side of a tape using a flexographic press. When two printed layers are used, the first consists of printed indicia and the second of a background layer which is patterned to leave the adhesive exposed at the edges of document-containing articles which are to be cut from the tape. The background layer functions to mask the adhesive so as to render it non-adhesive at the printed areas. In one embodiment, additional spaced patterns 56 (FIGS. 12 and 13) are printed on the adhesive to function as corner lift tabs when the tape is cut into individual articles. However, the great majority of the cutting of the tape is done directly through the adhesive at unprinted areas thereof, thereby leaving unprinted adhesive directly exposed at the side edges of the tape.

In U.S. Pat. No. 4,068,028 to Samonides, indicia are printed on the adhesive layer of transparent pressure-sensitive labels. These indicia are visible but "buried" and protected when the labels are applied to a mounting surface. In a variant, the labels are opaque, and indicia are printed both on the adhesive layer and on the face side of the label. When the label is mounted on the inner side of a glass window or the like, the indicia on the adhesive side are visible from the exterior side of the window and the indicia on the face side are visible from the interior side.

In U.S. Pat. No. 4,107,811 to Imsande, a tacky floor mat consists of a stack of adhesive-coated sheets peelably joined to each other. To provide lift tabs for the sheets, "a thin coating of non-adhesive material 18 is print-deposited" (col. 3, line 61) in a pattern on the adhesive-coated web material from which the sheets are to be cut. The adhesive-coated web material with the patterned coating 18 thereon is then laminated to itself to form a multilayer web (presumably with the pattern of non-adhesive material 18 maintained in register, layer to layer). The laminated material is then cut to sheet size in such manner that the patterned non-adhesive material 18 ends up at the corners of the stacked sheets. The non-adhesive material may be of a different color than the sheets.

In U.S. Pat. Nos. 4,671,003 and 4,787,158 to Vitol, removable pressure-sensitive sign stock is backed with release liner which has been perforated at regular intervals, the perforations being in the form of round openings where the adhesive is exposed. Talc or other adhesive masking material is applied to the adhesive at the areas of these openings, and the stock is then slit in both directions to form individual signs of rectangular or other shape each having one or more starting tabs at one, two or four corners. Circular labels are also disclosed having wedge-shaped non-adhesive areas, but how the corresponding perforations in the liner relate to the circular label shape, and how the circular labels are formed from the label stock is not apparent.

Various fingerlift arrangements specific to diaper tabs are also known in the prior art. One simple arrangement is to provide an adhesive-free zone at the fingerlift edge, as in U.S. Pat. No. 3,833,456 to Reed et al. This fingerlift edge can be difficult to grasp; there is no clear indication of the presence of a fingerlift, and the unsupported edges of rolls from which such tabs are cut can be easily damaged.

Another fingerlift arrangement for a diaper tab is a fold-over arrangement, as in U.S. Pat. No. 3,893,460 to Karami. If such folding-over is done during manufacture of the diaper fastener stock, differences in thickness are created across the width of the stock, causing distortions when the stock is rolled up for storage and shipment. On the other hand, if the folding-over is delayed only to be attempted on the diaper line, the difficulty of performing that step as part of the fastener dispensing and application procedure on the diaper line presents a risk of line stops and delays in diaper production.

Another known fingerlift arrangement for a diaper tab is a strip lamination, as in U.S. Pat. No. 4,726,971 to Pape et al. The laminated strip extends outwardly of the width of the diaper fastener stock, so that when the same is rolled and transported, the laminated strip can be easily damaged. Also, the strip creates local thickness variations in the roll.

Still another arrangement is a pull string, as in U.S. Pat. No. 4,005,713 to Mesek. This too may cause thickness variations, and may be complicated to fabricate and manipulate, particularly at high diaper line speeds.

SUMMARY OF THE INVENTION

Like the first six prior-art references listed above, the present invention also involves the making of articles from pressure-sensitive adhesive tapes in which the layer of pressure-sensitive adhesive is partially covered with a printed pattern of an adhesive barrier or ink. However, in the present invention as it relates to transfer tapes, the printing is along a continuous zone or line, and the tape is formed in whole or in part by slitting along that continuous line through the tape substrate, an adhesive coating, and the printed barrier. In the present invention as it relates to diaper tabs, an adhesive barrier or ink is used to form end fingerlifts for the tabs.

In one aspect, the present invention involves the concept of utilizing such means to eliminate or minimize complications, constraints and disadvantages involved in pattern-coating substrates with pressure-sensitive adhesive in the manufacture of transfer tapes and other articles. In particular, the invention minimizes or eliminates complications, constraints and disadvantages involved in the need to pattern-coat the adhesive as it is applied in order to allow slitting at one or more intermediate locations across the width of the line to define a specific tape width or widths, and in order to provide adhesive-free and therefore "pick"-free roll edges.

The invention overcomes the present inability to slit rolls of premanufactured transfer tape stock to various widths on demand, and eliminates the corresponding need to manufacture and inventory various widths of transfer tape pending demand for one or the other specific width or widths. The invention enables the manufacture of tape stock and tapes of substantially uniform thickness from one edge to the other, with attendant advantages to the manufacturer and converter.

In another aspect, the invention provides for the manufacture of diaper fastener-tab stock, and diaper fastening tabs formed from such stock, in a manner compatible with current diaper manufacturing practice, providing improved diaper tabs, and improved tabbed diapers, at little or no increase in costs over the practices of the prior art.

In this respect, the present invention provides diaper tab fasteners having fingerlifts (i.e., end tabs for the tab fasteners themselves) which are "built-in," which are easy and convenient to use, which overcome the problems of the prior-art diaper tab fingerlifts listed above, and which offer new advantages including the ability to economically provide improved distinguishability of the fingerlifts from the remainder of the tabs, the ability to provide for the absorption of finger oils or other contaminants, and the ability to add fragrances to the tabs.

In respect of the manufacture of diaper fastener-tab stock with "built-in" end tabs, the invention provides a variant or alternative to the design of diaper fastener-tab with built-in end tab taught in U.S. patent application Ser. No. 07/710, 692, filed Jun. 5, 1991, of common assignee, now abandoned.

DETAILED DESCRIPTION

The features and advantages of the invention will be more fully understood from the following description of specific examples, together with the drawings, in which:

FIG. 1 is a schematic isometric view illustrating certain prior art coating and slitting practices.

FIGS. 2 and 3 are similar views illustrating coating and slitting practices according to the present invention.

FIG. 9 may also be interpreted as a side elevation view of an individual diaper tab cut from the combined stock.

FIG. 15 may also be interpreted as a side elevation view of an individual diaper tab cut from the combined stock.

Figure 4:
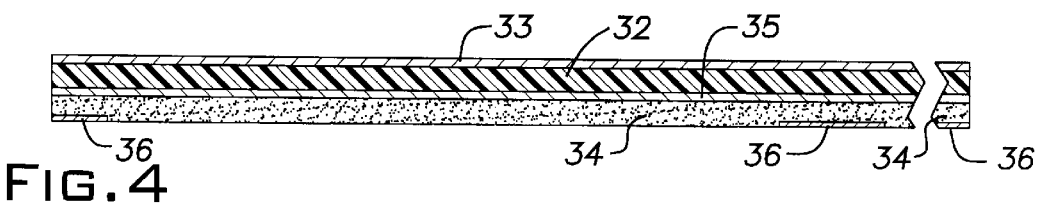
FIG. 4 is a broken cross-sectional view taken along plane 4—4 in FIG. 2, and inverted 180 degrees.

The coating and slitting shown highly schematically in FIG. 1 illustrates prior practices in the manufacture of transfer tape. A roll 10 may comprise a web of release liner substrate 12 which is coated on both sides with release coatings (not shown) either in prior coating operations before the forming of roll 10 or as initial coating and drying steps (not shown) following off-feed from roll 10.

At an adhesive-applying station A, a patterned adhesive coating 14 is applied to the substrate 12. The patterning results in a well-known manner from the use of die deckeling or the use of pattern bars (not shown) to prevent or minimize the application of adhesive along lines or zones 16 which are free or relatively free of adhesive.

The stock with its patterned adhesive coating is then slit by the slitters 18 into individual transfer tapes, and self-wound to form rolls of specific widths, such as the three individual rolls 21–23 in the illustration. The slitting occurs along the absolutely or relatively adhesive-free lines or zones 16. Slitting may also be performed at the adhesive-free side edges if edge trimming is required, but slitting at only the central locations is shown to simplify the illustration.

In accordance with well-known practice, the release coating (not shown) on the adhesive-carrying side of the substrate 12 is chosen to give a higher or harder release than the release coating (not shown) on the opposite or exposed side of the substrate. When each tape is self-wound into roll form, the adhesive associated with one turn of substrate contacts the exposed side of the preceding turn of substrate which bears the release coating which allows relative low or easy release. The result is that when the roll is subsequently unwound, the adhesive layer remains associated with the same length of substrate on which it was coated even though there is a release coating (the one of relatively higher or harder release) between the adhesive and that same length of substrate.

The adhesive face of the tape then can be applied to label facestock or to another object intended to be adhesively mounted in its end use, and the adhesive 14 permanently adheres thereto. The substrate 12 then functions as a release liner protecting the adhesive 14 until the liner is removed and the label or other object is adhered to its final mounting.

This final removal of the liner utilizes the relatively higher or more difficult release action of the release coating on the adhesive-bearing side of the substrate 12.

The prior-art procedures described above and illustrated in FIG. 1 in highly schematic form require that the adhesive coating be patterned as it is applied in accordance with the specific tape width or widths desired. This means that adhesive-coated transfer tape stock cannot be premanufactured and inventoried, to be slit to various widths on demand. Instead, all widths expected to be eventually sold must be patterned at the time the adhesive is applied, and widths of various sizes then held in inventory pending eventual sale. Such inventory consists of tape stock that has at least been patterned to width. Slitting to width may be performed in the same pass as patterning, or may be delayed up until time of sale. Some widths may sell more slowly than expected, and others faster, presenting the necessity of maintaining whatever inventory is "thrust on" the manufacturer by reason of bad guesses as to demand for various widths. For example, in the example illustrated in FIG. 1, the operation illustrated may be carried out as a result of an order for tape of the width of roll 21, an intermediate width.

Relatively narrow tape roll 22 and relatively wide tape roll 23 (or the patternings for such rolls when slitting is performed at a later pass) result as byproducts, so to speak, of the manufacture of tape roll 21 and are a product of the manufacturer's best guess as to the market for tapes of various sizes, and must be inventoried until tapes of those specific sizes are in fact ordered.

Another disadvantage of prior art practice is the fact that it is rather complicated to reset a coating operation as required by changes in tape widths to be cut. Each change requires redeckeling a die or resetting a pattern bar.

The relatively or absolutely adhesive-free lines or zones 16 present another problem in that the thickness of the stock is considerably less at these zones than on the portions of the stock bearing the adhesive layer 12. Thus, the stock at the edges of the rolls 21–23 is substantially thinner than at the central portions of the rolls, so that the stock is firmly wound on itself, layer-to-layer, only at the central portions and not at the edges. The stock at the edge portions is therefore subject to being readily deformed and damaged by accidental contact with any solid object.

In one aspect of the invention, these complications, constraints and disadvantages of prior-art practice may be largely or wholly eliminated. Thus, in the manufacture of transfer tape as illustrated in FIG. 2, a roll 30 may again be provided comprising a web of release liner substrate 32 which again is coated on both sides with release coatings (not shown in this view) either in prior coating operations before the forming of roll 30 or as initial coating and drying steps (not shown) following off-feed from roll 30.

However, at the adhesive-applying station A, a layer of adhesive 34 is applied to the substrate 32 continually across the width of the substrate 32. The adhesive-coating step may be performed in the absence of any patterning, as shown, or less preferably there may be patterning at the side edges.

Following application of the adhesive layer 34, adhesive-inhibiting masking 36 is applied at a printing station P. The masking may be an ink applied with a flexographic printing press or laser printer (not shown), whose positions across the width of the adhesive coating 34 may be readily adjusted as desired to thereby determine tape width. Preferably, the masking is applied at the side edges, as shown, as well as at an intermediate portion or portions of the web.

Following drying of the ink or masking, employing drying means if required (not shown), the adhesive-coated stock is then slit by the slitter 38. Slitting may also be performed at the side edges if edge trimming is required, but slitting at only the central location is shown to simplify the illustration. The slit stock is then self-wound to form the individual transfer tape roll 41, and the reserve roll 44 of adhesive-coated stock. The stock in the reserve roll 44 is not "committed" to specific roll widths, such as the relatively narrow width of the roll 22 or to the relatively wide width of the roll 23 as in the prior-art example of FIG. 1.

If, at a later time, an order is received for one of the latter widths, or any other width less than that of the reserve roll 44, the reserve roll can be processed as illustrated in FIG. 3. Thus, the adhesive-coated reserve roll 44 is unwound and passed through a printing station P to receive the adhesive-inhibiting masking 36a. The lateral location of the print cylinders or jets (not shown) is readily adjusted to produce the masking at the desired location across the width of the reserve roll 44, as opposed to the laborious process of redeckeling a die or readjusting a pattern bar, either of which involves resetting the coating operation.

Following drying of the masking, employing drying means if required (not shown), the stock is then slit by the slitter 38a. Thus a roll 42 of narrow width is produced pursuant to a specific order, and also a roll 43 which, if not sold, may be inventoried for possible later sale at that width, or at narrower widths after further slitting.

Figure 5:
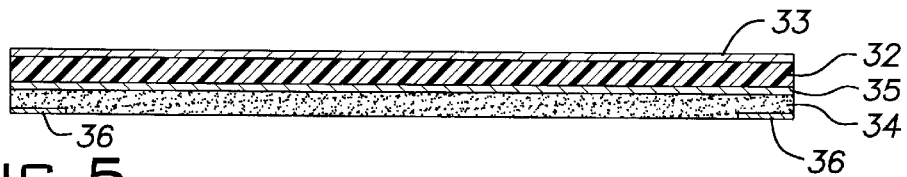
FIG. 5 is a cross-sectional view of an individual tape slit from the stock of FIG. 4.
Figure 6:
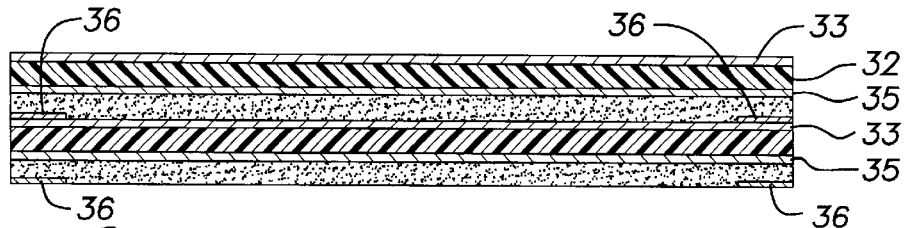
FIG. 6 is a view similar to FIG. 5, but showing two adjacent layers of the tape of FIG. 5, with one layer superposed on the other, and thus illustrating two layers of the tape as they would appear in a cross-sectional view of a roll of the tape.

FIGS. 4 to 6 illustrate the novel tape stock and tape of the invention in greater detail. FIG. 4 is a cross-sectional view, partly broken, taken on plane 4—4 of FIG. 2 and inverted 180 degrees. The easier or lower release coating 33 and higher or harder release coating 35 are shown. FIG. 5 is a cross section of the slit individual tape which is self-wound into the roll 41. FIG. 6 shows two adjacent wraps or turns of the roll 41. While these figures are not to scale, they do give a rough idea of the insignificant effect of the printed adhesive-inhibiting masking 36 on the overall thickness of the tape. As suggested in FIGS. 4–6, the tapes are substantially uniform in thickness from edge to edge. Preferably, the thickness of the masking means is less than 1% of the combined thickness of the associated substrate and substrate adhesive. Actual typical thicknesses which have been used are, for example, (microns): substrate 120, adhesive layer 30, release coats (each) 1, ink or masking 0.4.

As particularly suggested by FIG. 6, the edge portions of the tape rolls are substantially as tightly wound as the center portions, with firm layer-to-layer support between the various turns of the roll out to the very edges of the roll.

In sum, the thickness of the masking means is a small percentage of the combined thickness of the associated substrate and substrate adhesive, preferably less than 1%, the tape or diaper fastener stock has a substantially uniform edge-to-edge thickness, the stock may be tightly rolled, and the layer edges at both sides of rolls of the stock are solidly supported by adjacent layer edges.

Converters of tapes and other products using the printed adhesive masking of the present invention can handle the adhesive tapes or stocks efficiently. The rolls can be tightly wound. There is little or no cutting differential between masked and unmasked adhesive areas. The rolls unwind in a uniform manner. The risk of edge damage (nicking) of the rolls is reduced.

As described above, in the foregoing examples of the invention, the printing of the adhesive barrier is along a continuous zone or line, and the tape is formed in whole or in part by slitting along that continuous line through the tape substrate, an adhesive coating, and the printed barrier.

(All the capitalized names of products used in the following descriptions of maskings, release coatings, liner, and adhesives are proprietary trademarks or trade names of the indicated manufacturers or suppliers.)

Various adhesives have been used in transfer coating in the past as illustrated in FIG. 1, and in general any such adhesive can be adapted to the invention. For example, the adhesive may be a thermally cross-linked acrylic adhesive, the cross-linking mechanism comprising a metal chelate such as aluminum acetylacetonate (in a small weight percentage, say 0.15%).

A suitable masking for such adhesive may be formed by printing, using as the ink FLEXO WRITE ON WHITE CLA 30357 ink supplied by Sun Chemical Corp. The ink may be thinned with a press solvent to a running viscosity of 20–22 seconds as measured using a No. 2 Zahn Cup. The solvent may be a mixture of 75% normal propyl alcohol, 25% ethyl acetate and 5% EKTOSOLVE (Chemcentral, ethylene glycol monoethyl ethyl ether).

The following has been used for the lower or easier release coating 33, in weight percentages:
  96.10% Dow SYLOFF 7044 (100% solid, rhodium precatalyzed organofunctional siloxane easy release polymer)
  3.90% Dow Q2-7048 (100% solid reactive polymethylhydrogen siloxane, crosslinker polymer)
This coating was applied at 1.5 grams per square meter.

The following has been used for the higher or harder release coating 35:
  51.00% Dow SYLOFF 7044 (100% solid, rhodium precatalyzed organofunctional siloxane easy release polymer)
  44.50% Dow Q2-7069 (100% solid, rhodium precatalyzed organofunctional siloxane high release polymer)
  4.50% Dow Q2-7048 (100% solid reactive polymethylhydrogen siloxane, crosslinker polymer)
This coating was applied at 1.4 grams per square meter.

A suitable choice for liner in the practice of the invention as above described is 80# SUPER TOUGH paper (Otis Paper).

Similar practices may be utilized in the manufacture of improved diaper fastener-tab stock adapted to be supplied to a diaper manufacturer and to be separated by the manufacturer into individual diaper-fastening tabs and applied to individual diapers, usually two tabs to a diaper for infants, and two to six for adults.

Figure 8:
FIG. 8 is a view similar to FIG. 7 and showing additional tape stock used with the stock of FIG. 7.
Figure 9:
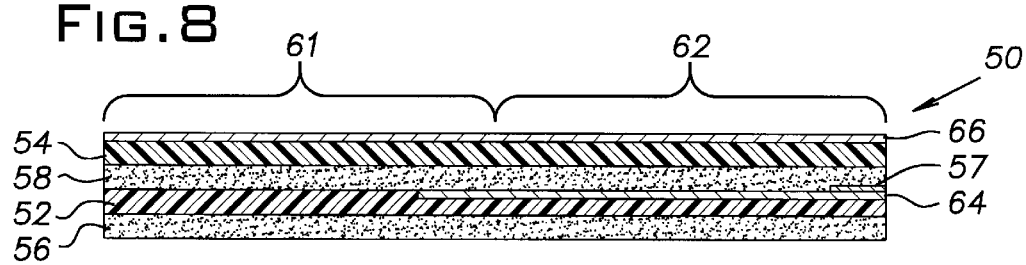
FIG. 9 is a cross-sectional view of the tape stocks of FIGS. 7 and 8 combined with each other.

The individual fastener 50 seen in FIG. 9 is, in effect, a cross-sectional view of the diaper fastener stock from which the individual fastener has been formed by transverse cuts. This stock, then, consists of initially flat but flexible first and second substrates 52 and 54 suitable to be formed in long passes along the machine direction (into the paper as viewed in FIGS. 7–9) of a coating and laminating line without the necessity for folding operations and completely by web coating, slitting and web-to-web laminating operations, and suitable for high-speed dispensing on automatic equipment. The substrates may be polypropylene film 4.6 mils in thickness, for example.

The first or anchoring substrate 52 bears first substrate adhesive 56 on its underside. The first substrate 52 and the first substrate adhesive 56 extend, transversely to machine direction, along first and second length portions 61 and 62 of the web construction, respectively.

The second or additional substrate 54 bears second substrate adhesive 58 on its underside and also extends along the first and second length portions 61 and 62. Release means for the adhesive 58 of the second substrate 54 is carried on the first substrate 52 and may be a release coat 64. This release means extends along the second length portion 62 but not significantly along the first length portion.

The first and second substrate adhesives may have the following formulation:
  31.7% KRATON 1107 (Shell Chemical, polystyrene-isoprene-polystyrene linear block copolymer)
  46.3% ESCOREZ 1310LC (Exxon Chemical, solid $C_5$ tackifying resin)
  19.8% WINGTACK 10 (Goodyear Chemical, solid $C_5$ tackifying resin)
  1.0% ETHANOX 330 (Ethyl Corp., phenolic anti-oxidant)
  1.2% PLASTONOX LTDP (American Cyanimid, thioester anti-oxidant)

A suitable masking or barrier may be formed by printing, using as the ink SUNTEX 182 PINK CLA 40457F ink supplied by Sun Chemical Corp. The ink may be thinned with the same press solvent given previously, to the same running viscosity.

Figure 7:
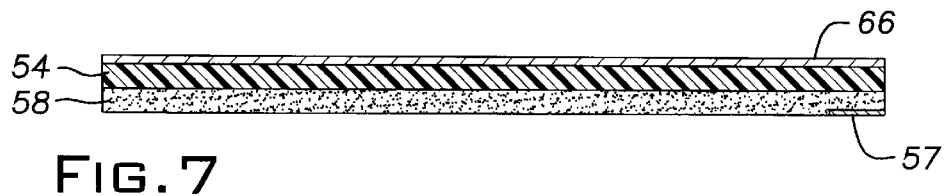
FIG. 7 is a cross-sectional view similar to FIG. 5 and showing tape stock for the manufacture of diaper tabs according to the invention.

The second substrate construction as seen in FIG. 7 is formed in a manner similar to the formation of the tape seen in FIG. 5. The substrate 54 is formed from a substrate twice as wide by slitting after being coated with the adhesive 58 and after adhesive barrier means 57 is printed on the adhesive along a continuous zone or line at the midline of the original or unslit substrate.

Preferably, the barrier means 57 is an ink or other barrier of a color which contrasts with the color of the adhesive. (If desired, the substrate 54 may be provided at its corresponding edge with corresponding coloring, not shown, which contrasts with the remainder of the substrate. This can be done by known printing or coextrusion techniques. Slitting produces two tapes, mirror images of each other, one of which is the tape seen in FIG. 7, which includes the adhesive masking portion 57.

The first substrate portion as seen in FIG. 8 is formed by conventional coating techniques and may also represent a half-width of original substrate stock slit down the middle. The tapes as seen in FIGS. 7 and 8 can be cut from original or unslit substrates which are combined prior to slitting, or can be combined following slitting of the original or unslit substrates. In any event, when the constructions of FIGS. 7 and 8 are laminated together to form the diaper fastener stock illustrated in FIG. 9, the masking portion 57 is contained snugly within the associated end of the lamination to provide built-in end tab means.

Suitable release means may be provided to allow the construction as so far described to be self-wound for storage and shipment. Such release means may be a release coat 66 on the second substrate 54. When the diaper fastener stock is wound on itself, the first substrate adhesive 56 is releasably supported against the release coat 66, and readily separates therefrom when the roll is subsequently unwound on a diaper manufacturing line.

When the diaper fastener stock is wound as just described, the built-in end tab afforded by the masking portion 57 and associated overlying portion of substrate 54 allows the roll to form evenly without build-up of one side, and presents evenly thick edges which are supported from one turn to the nest in the wound roll.

Figure 10:
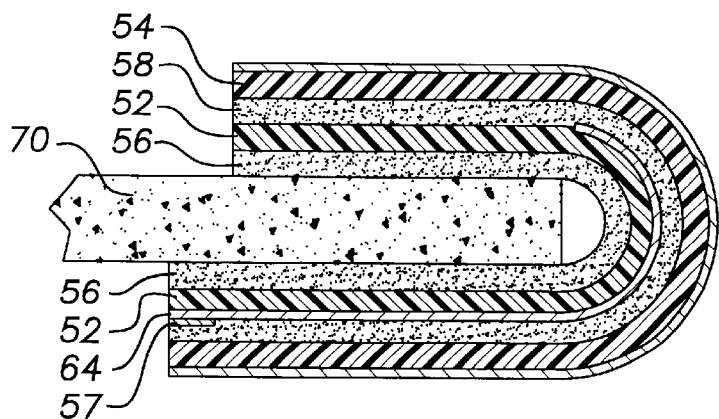
FIG. 10 shows an individual tab corresponding to the construction of FIG. 9 applied around the edge of a diaper.

On the manufacturing line, the diaper fastener stock is unwound and cut transversely to form a series of individual fasteners which are applied, usually in pairs, to individual diapers by being folded around a diaper edge. FIG. 10 shows an individual fastener cut from the stock described above applied around the edge of a diaper 70. This is the undeployed condition of the diaper fastener. Fasteners made according to the invention have been found to perform satisfactorily when applied to HUGGIES SUPER TRIM DIAPERS (Kimberly Clark) which, as is typical of many contemporary disposable diaper constructions, have a fastener-receiving frontal tape to reinforce the relatively fragile and easily torn diaper outer plastic shell or envelope.

Figure 11:
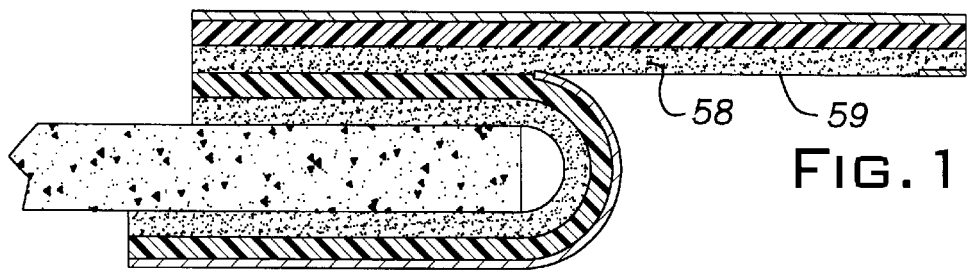
FIG. 11 shows the same tab deployed for fastening to another part of the diaper.

FIG. 11 illustrates the deployed condition of the diaper fastener. When a diaper is applied to an infant or other person, each diaper fastener is moved from undeployed to deployed condition. The second length portion of the second substrate 54 constitutes deployment means separable from the second length portion of the first or anchoring substrate 52 for deployment as shown in FIG. 11 and adherence to another portion of the diaper (not shown) by application of the exposed second length portion of the second substrate adhesive 58 to such other diaper portion. The end-tab means comprising masking portion 57 is at the free end of such deployment means.

In other words, the second substrate 54 will be seen to constitute substrate means which has an inner and an outer end, and which is fastened at its inner end to one part of the diaper via the adhesive layers 56 and 58 and the substrate 52 (FIG. 10). The tape will be seen to have a pressure-sensitive adhesive face 59 (FIG. 11) at least at the outer end of such substrate means, such face being carried on release means 64 which in turn is carried on the same part of the diaper via the substrate 52 and adhesive 56 (FIG. 10). The second substrate is adapted to have its outer end peeled from and thereby deployed from the part of the diaper seen in FIGS. 10 and 11 for fastening to another part of the diaper (not shown) to thereby establish a user joint and fasten the diaper. The outer end of the second substrate has lift tab means in the form of the masking portion 57 for initiating peeling of the outer end from the release means 64.

The barrier means or masking portion may, if desired, be provided with fragrances, which may simply be added to a printing ink. Absorbent powders in the ink may function to pick off finger oils of the parent or other caregiver who handles the diaper tab, thereby reducing the likelihood of contamination of the bonding interface established when the tab is fastened. The ingredients of the barrier or masking may have a double function, for example an absorbent powder may contribute both to deactivating or masking the pressure-sensitive adhesive and to absorbing finger oils.

Figure 12:
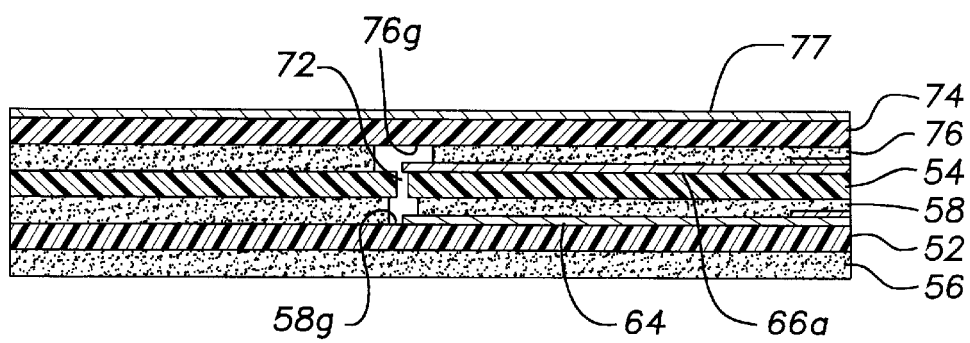
FIG. 12 is a view similar to FIG. 9 and showing a different form of diaper tab embodying the invention.
Figure 13:
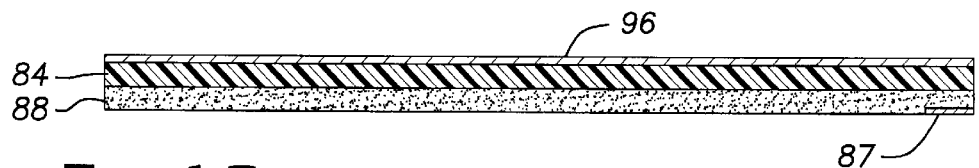
FIG. 13 is a cross-sectional view similar to FIG. 7 showing tape stock for the manufacture of another form of diaper tabs according to the invention.
Figure 14:
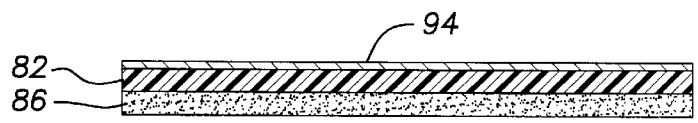
FIG. 14 is a view similar to FIG. 13 and showing additional tape stock used with the stock of FIG. 13.

Many variations in the specific example described above are possible. FIG. 12 shows a variant in which the invention is incorporated in a diaper fastener of the general type shown in U.S. Pat. No. 4,020,842 to Richman et al. the disclosure of which is incorporated by reference as if fully repeated herein. This type of fastener has more than one additional substrate and correspondingly more than one deployment means. In the construction of FIG. 12, a first or anchoring substrate 52 and a second or additional substrate 54, and associated first and second substrate adhesives 56 and 58, are provided similarly to the construction of FIG. 9. Further, a third substrate 74 (constituting a second additional substrate) is provided along with associated third substrate adhesive 76. Since this substrate is the outermost in this construction, a release means such as the release coat 77 is provided along the entire length of the substrate for self-winding purposes. The release coat 66 of the FIG. 9 construction is replaced by shortened release coat 66a which extends along the second length portion corresponding to length portion 62 in FIG. 9, but not significantly along the first length portion corresponding to length portion 61 in FIG. 9. Preferably, the substrate adhesives 58 and 76 are interrupted at the fold-around portion of the diaper fastener by adhesive gaps 58g and 76g.

The second substrate 54 of the FIG. 12 construction is interrupted by a slit or small gap 72. The general operation of the construction in the manner of deployment, reopening and reclosing is the same as that of the aforesaid Richman et al. patent. However end-tab means of the general kind intended by the present invention is provided on at least one of the deploying substrates. In this case, end-tab means comprising the printed masking portion 57a is provided in association with the free end of substrate 54, and end-tab means comprising the printed masking portion 57b is provided in association with the free end of substrate 74.

Still other forms of diaper fasteners utilizing the invention may be provided. Thus a type of two-substrate tab may be provided wherein both substrates perform an anchoring function, and less substrate material is used than in the designs previously described.

Such diaper tab stock may be first combined on the diaper manufacturing line from stock components made by different manufacturers. For example the two substrates and associated adhesives and release coats may be provided in self-wound form from different sources or from a single source.

Thus as shown in FIGS. 13–17, first and second substrates 82 and 84 are provided with first and second substrate adhesives 86 and 88, and release coats 94 and 96 are provided on the first and second substrates. In the industry, the first and second substrates together with associated adhesives and coatings are often referred to respectively as release tape stock and fastener tape stock. The diaper manufacturer combines the release tape stock or substrate 82 and the fastening tape stock or substrate 84 in the manner shown in FIG. 15, then cuts the combined tape stock into individual fastener tapes and applies successive fasteners around a diaper edge in the manner seen in FIG. 16. Fastener tapes for the opposite side edge of the diaper are formed and combined in the mirror image of the illustrated tape.

Figure 16:
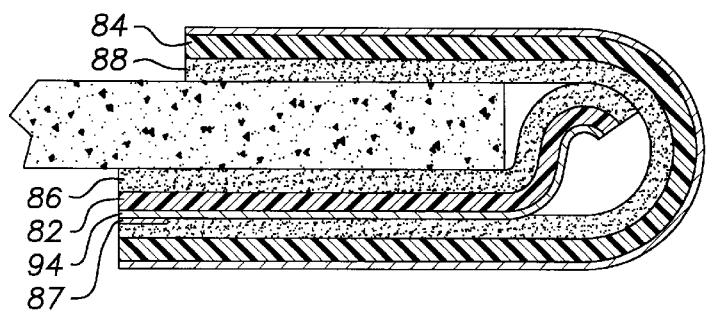
FIG. 16 shows an individual tab corresponding to the construction of FIG. 15 applied around the edge of a diaper.
Figure 17:
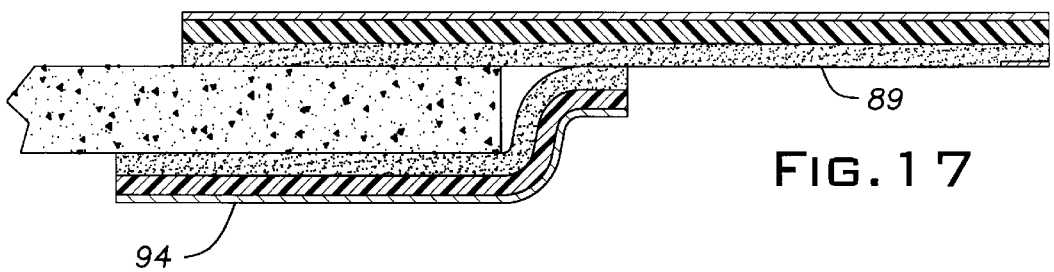
FIG. 17 shows the same tab deployed for fastening to another part of the diaper.

The second substrate 84 will be seen to constitute substrate means which has an inner and an outer end, and which is directly fastened at its inner end to one part of the diaper by the adhesive layer 88. (FIG. 16). The tape will be seen to have a pressure-sensitive adhesive face 89 (FIG. 17) at least at the outer end of such substrate means, such face being carried on release means 94 which in turn is carried on the same part of the diaper via the substrate 82 and adhesive 86 (FIG. 16). The second substrate is adapted to have its outer end peeled from and thereby deployed from the part of the diaper seen in FIGS. 16 and 17 for fastening to another part of the diaper (not shown) to thereby establish a user joint and fasten the diaper. The outer end of the second substrate has lift tab means in the form of the masking portion or barrier means 87 for initiating peeling of the outer end from the release means 94.

Figure 15:
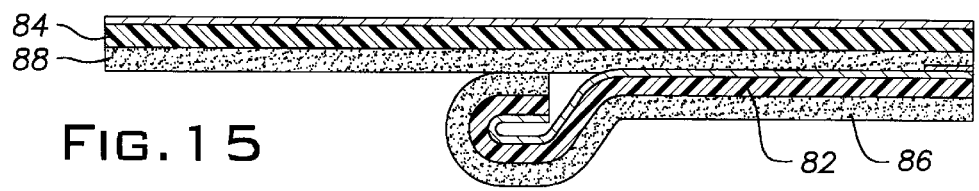
FIG. 15 is a cross-sectional view of the tape stocks of FIGS. 13 and 14 combined with each other.

In this construction, the release coat 94 serves two release functions; it allows self-winding of the substrate 82 for shipment from the tape stock manufacturer to the diaper manufacturer and it serves as the release face against which the adhesive face 89 is stored in the conditions shown in FIGS. 15 and 16. The release coat 96 performs the single release function; it allows self-winding of the substrate 84 for shipment.

The various slitting, patterning and combining operations at the fingerlift end of the diaper fastener stock can be performed in duplicate at the web center on a stock manufacturing line, with the slitting, patterning and combining on one lateral side of the infed webs being done in mirror image to the same operations on the other side. In such case, of course, the width of the infed webs is at least double the width of the resulting diaper fastener stock.

It is to be noted that in all instances the end-tab means is located within the length of the longest of the one or more additional or deployment substrates.

The result is a diaper tab fastener with a fingerlift superior to those of the prior art discussed above. The end-tab means of the invention can be readily and conveniently grasped and manipulated by the person applying the diaper. The end-tab means can be readily fabricated on a diaper fastener stock production line by simple patterning and slitting steps that are fully compatible with economical high speed production. The stock can be self-rolled in smooth, uniform rolls that are free of local high spots and resulting distortions.

The invention is not limited to the specific details of the disclosed embodiments, but is defined in the following claims.

What is claimed is:

1. In a diaper having adhesive fastener tapes, each fastener tape having a width and being cut from fastener tape stock having a length, said cut being such that the width direction of the fastener tape corresponds to the length direction of the stock, each fastener tape having substrate means for providing a substrate, said substrate means having an inner and an outer end and being fastened at its inner end to one part of the diaper, each tape having a pressure-sensitive adhesive face at least at the outer end of said substrate means, said adhesive face being carried on release means for providing a release face, said release means in turn being carried on said one part of the diaper, said substrate means being adapted to have its outer end peeled from and thereby deployed from said one part of the diaper for fastening to another part of the diaper to thereby establish a user joint and fasten the diaper, said adhesive face being liftably peelable from said release face of said release means to effect said deployment, the outer end of said substrate means having an easy-start peelback lift tab for initiating said peeling of said outer end, the improvement comprising providing said easy-start peelback lift tab in the form of a printed adhesive-inhibiting liftable masking means for inhibiting adherence of the adhesive face, said outer end of said substrate means having an outermost part, said printed masking means being provided on the adhesive face at said outermost part of said outer end, said printed masking means being in contact with said release face, said printed masking means extending across said width of said tape whereby said printed masking means is cut from a printed masking means continuum extending along the length of said fastener tape stock, said printed masking means being peelable and liftable from said release face along with said adhesive face for easy-start initiation of said peeling from said one part of the diaper, and said printed adhesive-inhibiting liftable masking means including therein a fragrance.

2. In a diaper having adhesive fastener tapes, each fastener tape having a width and being cut from fastener tape stock having a length, said cut being such that the width direction of the fastener tape corresponds to the length direction of the stock, each fastener tape having substrate means for providing a substrate, said substrate means having an inner and an outer end and being fastened at its inner end to one part of the diaper, each tape having a pressure-sensitive adhesive face at least at the outer end of said substrate means, said adhesive face being carried on release means for providing a release face, said release means in turn being carried on said one part of the diaper, said substrate means being adapted to have its outer end peeled from and thereby deployed from said one part of the diaper for fastening to another part of the diaper to thereby establish a user joint and fasten the diaper, said adhesive face being liftably peelable from said release face of said release means to effect said deployment, the outer end of said substrate means having an easy-start peelback lift tab for initiating said peeling of said outer end, the improvement comprising providing said easy-start peelback lift tab in the form of a printed adhesive-inhibiting liftable masking means for inhibiting adherence of the adhesive face, said outer end of said substrate means having an outermost part, said printed masking means being provided on the adhesive face at said outermost part of said outer end, said printed masking means being in contact with said release face, said printed masking means extending across said width of said tape whereby said printed masking means is cut from a printed masking means continuum extending along the length of said fastener tape stock, said printed masking means being peelable and liftable from said release face along with said adhesive face for easy-start initiation of said peeling from said one part of the diaper, and said printed adhesive-inhibiting liftable masking means including therein oil-absorbing means for absorbing finger oils.

\* \* \* \* \*

UNITED STATES PATENT AND TRADEMARK OFFICE
CERTIFICATE OF CORRECTION

PATENT NO.   : 6,365,793 B1
DATED        : April 2, 2002
INVENTOR(S)  : Thomas L. McLaughlin et al.

It is certified that error appears in the above-identified patent and that said Letters Patent is hereby corrected as shown below:

<u>Title page,</u>
Item [56], References Cited, U.S. PATENT DOCUMENTS, please include the following references:

| | | | |
|---|---|---|---|
| -- | 3,159,930 | 6/1963 | Allen et al. |
| | 3,833,456 | 9/1974 | Reed et al. |
| | 3,874,893 | 4/1975 | Cherrin |
| | 3,893,460 | 7/1975 | Karami |
| | 4,005,713 | 2/1977 | Mesek |
| | 4,068,028 | 1/1978 | Samonides |
| | 4,107,811 | 8/1978 | Imsande |
| | 4,671,003 | 6/1987 | Vitol |
| | 4,726,971 | 2/1988 | Pape et al. |
| | 4,787,158 | 11/1988 | Vitol -- |

Signed and Sealed this

Fourth Day of February, 2003

JAMES E. ROGAN
*Director of the United States Patent and Trademark Office*